(12) United States Patent
Angles Cano et al.

(10) Patent No.: US 8,541,189 B2
(45) Date of Patent: Sep. 24, 2013

(54) METHOD FOR MEASURING THE PLASMINE ACTIVITY OF MICROPARTICLES PRESENT IN A SAMPLE OF BLOOD OR A BLOOD COMPONENT

(75) Inventors: Eduardo Angles Cano, Paris (FR); Romaric Lacroix, Marseilles (FR); Florence Malaterre, Marseilles (FR); Françoise Dignat-George, Marseilles (FR)

(73) Assignees: Institut National de la Sante et de la Recherche Medicale (Inserm), Paris Cedex (FR); Assistance Publique—Hopitaux de Marseille, Marseille Cedex (FR); Universite d'Aix-Marseille, Marseille Cedex (FR); Universite de caen Basse-Normandie, Caen Cedex (FR)

( * ) Notice: Subject to any disclaimer, the term of this patent is extended or adjusted under 35 U.S.C. 154(b) by 635 days.

(21) Appl. No.: 12/663,393

(22) PCT Filed: Jun. 6, 2008

(86) PCT No.: PCT/FR2008/000767
§ 371 (c)(1),
(2), (4) Date: May 25, 2010

(87) PCT Pub. No.: WO2009/004189
PCT Pub. Date: Jan. 8, 2009

(65) Prior Publication Data
US 2010/0260724 A1    Oct. 14, 2010

(30) Foreign Application Priority Data

Jun. 7, 2007   (FR) ..................................... 07 04060

(51) Int. Cl.
*C12Q 1/56* (2006.01)

(52) U.S. Cl.
USPC ........................................................... 435/13

(58) Field of Classification Search
None
See application file for complete search history.

(56) References Cited

PUBLICATIONS

Graves et al., "Proinvasive Properties of Ovarian Cancer Ascites-Derived Membrane Vesicles", Cancer Research 64 : 7045-7049 (2004).*
Moser et al., "Specific binding of urinary-type plasminogen activitor (u-PA) to vitronectin and its role in mediating u-PA-dependent adhesion of U937 cells", Biochemical J. 307 : 867-873 (1995).*
Stief et al., "Functional determination of plasmin in arginine-stabilized plasma", Clinical and Applied Thrombosis/Hemostasis 11 (3) : 303-309 (2005), Abstract Only.*
Biro et al., "A flow cytometric method of microparticle analysis", J. Thromb. Haemost. 2 : 1843-4 (2004).*
Dignat-George et al., "Numeration of circulating microparticles of varios cellular origin by flow cytometry", J. Thrombo. Haemost. 2 : 1844-5 (2004).*
Lacroix et al., "Activiation of plasminogen into plasmin at the surface of endothelial microparticles: a mechanism that modulates angiogenic properties of endothelial progenitor cells in vitro", Blood 110 (7) : (Oct. 1, 2007), prepublished online Jul. 2, 2007.*
Orozco et al., "Flow Cytometric Analysis of Circulating Microparticles in Plasma", Cytometry Part A 77A: 501-514 (2010).*

* cited by examiner

*Primary Examiner* — Sandra Saucier
(74) *Attorney, Agent, or Firm* — Browdy and Nemark, PLLC

(57) ABSTRACT

The invention relates to a method for measuring the plasmine activity of microparticles, in particular circulating microparticles, in a sample of a biological fluid, particularly a biological fluid in a flow situation, wherein said method can be used as a diagnosis method or a method for following a treatment.

20 Claims, No Drawings

METHOD FOR MEASURING THE PLASMINE ACTIVITY OF MICROPARTICLES PRESENT IN A SAMPLE OF BLOOD OR A BLOOD COMPONENT

A subject of the invention is a method for measuring the plasmin activity of microparticles, in particular the circulating microparticles, present in a sample of biological fluid, in particular a biological fluid in a flow situation, or in a tissue extract, said method being able to serve as a diagnosis method or a method for monitoring a treatment.

The microparticles resulting from blebbings of the cell membrane have been described in various cell models and in numerous pathological conditions as reliable markers of cell activation and/or apoptosis.

In particular, the inventors initially described the release of these microparticles by the endothelial cells in response to an inflammatory stimulation and the increase in the quantity of circulating endothelial microparticles in patients at risk of thromboses. High levels of circulating endothelial microparticles have since been described in different pathological conditions such as coronary syndromes, renal failure, diabetes, antiphospholipid syndrome (APLS), thrombotic thrombocytopenic purpura (TTP) or also drepanocytosis, disorders in which the presence of microparticles reflects endothelial dysfunction and is indicative of a poor prognosis.

As microparticles express various bioactive components coming from the cells from which they originate, they can exhibit a wide range of biological activities capable of modifying functions of endothelial or blood cells, influencing vascular homeostasis and participating in inflammatory responses or angiogenesis.

For example, microparticles, in particular the circulating microparticles, have procoagulant phospholipid surfaces involved in the assembly and activation of the coagulation factors.

Similarly, the participation of microparticles, in particular the circulating microparticles, in the generation of thrombin results from their ability to express, transfer or induce tissue factor in the vascular compartment.

Among the main regulators of the haemostatic equilibrium, the plasminogen activation system is the main physiological route for dissolution of the fibrin clot. This route also facilitates angiogenesis by aiding the proteolysis of the components of the extracellular matrix.

The conversion of plasminogen to active plasmin depends on two serine proteases: tissue-type plasminogen activator (t-PA:) which in the vessels is mainly involved in fibrinolysis and urokinase-type plasminogen activator (u-PA;) which, bonded to its specific receptor, uPAR, is involved in pericellular proteolysis.

The generation of plasmin induced by uPA and the resultant activation of the matrix metalloproteinases (MMPs) promote the migration of cells through the interstitial matrix and participate in processes such as tissue remodelling, metastatic invasion and angiogenesis.

Uncontrolled and/or excessive activation of plasminogen can have detrimental consequences, inducing cell detachment and/or cell apoptosis. It is therefore understood that the regulation of the expression of the plasmin at the surface of the cells, in particular of the endothelial cells is of crucial importance in the regulation of vascular homeostasis.

On reading the above, it is therefore possible to understand the benefit which there is, on the one hand in being able to evaluate the generation of the "plasmin activity" of microparticles, in particular the circulating microparticles, in a biological fluid, in particular in a biological fluid in a flow situation, very particularly blood, or in tissue extracts and on the other hand being able to modify this activity.

By "biological fluid" is meant any extractable body fluid including for example blood, cerebrospinal fluid (CSF), bronchoalveolar fluid (BAF), urine, synovial fluid, breast milk, saliva, tears, seminal fluid, ascitic fluid, pleural effusion, amniotic fluid.

By "biological fluid in a flow situation" is meant any body fluid which flows within or out of the body naturally including for example circulating blood, breast milk, urine, saliva, tears, seminal fluid, the menstrual flow and any other serous and/or mucous flow.

Among the sources of tissue extract there can be mentioned atheromatous plaques or any other tissue obtained by surgery.

The term "plasmin activity" must be understood in the present text as meaning the ability of a sample of biological fluid, in particular a biological fluid in a flow situation, containing microparticles, in particular circulating microparticles, to generate plasmin, whatever the mechanism implemented.

By way of diagnostic method, measured in the biological fluid sample containing microparticles, in particular the circulating microparticles, and compared with the measurement of this same ability in a control sample obtained from so-called "normal" individuals, i.e. having no pathology, the value of the "plasmin activity of the tested sample", if it is significantly greater than that of the control will reflect for example and without limitation, for an individual, a greater or lesser risk of suffering for example vascular accidents caused by increased instability of the atheromatous plaques, a greater or lesser risk for an individual with cancer of suffering a metastatic invasion or also for an individual a greater or lesser risk of suffering a cerebral vascular accident and its harmful consequences for brain function. If this value of the "plasmin activity of the tested sample" is less than that of the control, then it will for example reflect an increased risk of thrombosis for an individual whose blood has been tested.

By way of monitoring a treatment, the value of the "plasmin activity of the tested sample" measured in the microparticles, in particular the circulating microparticles, in a biological fluid sample, in particular a biological fluid in a flow situation, from an individual undergoing treatment, and compared with the measurement of this same ability in a control sample obtained from the same individual before the treatment or earlier in the treatment, makes it possible to follow the evolution of the response of said individual as a function of the treatment administered to them.

However, a need still exists for a simple, effective and reliable test of the risks incurred by a patient, linked to too strong or too weak a plasmin activity of their blood or also a simple test monitoring the course of a treatment aimed at modifying the plasmin activity of the microparticles, in particular the circulating microparticles, in a biological fluid, in particular a biological fluid in a flow situation, of an individual.

It is one of the purposes of the present invention to provide such a test.

In fact, after prolonged work and in a surprising manner, the inventors have shown, to their knowledge for the first time, that the circulating microparticles present in a biological fluid, in particular a biological fluid in a flow situation, in particular in blood, of an individual, have a biological activity conferring upon them the ability to generate plasmin.

On the basis of this discovery, a subject of the present invention is a method for measuring the plasmin activity of microparticles, in particular the circulating microparticles, in a sample of biological fluid, in particular a biological fluid in a flow situation, in particular of blood, taken previously, in which in a first stage the microparticles, in particular the circulating microparticles, present in said sample are isolated, in a second stage, the ability of said microparticles isolated in stage 1 to generate plasmin is measured by any appropriate means and in a third stage the result of the measurement obtained in stage 2 is compared with the result of an identical measurement carried out under the same conditions on a control sample of identical biological fluid.

According to a variant of the invention, the control identical biological fluid can be a biological fluid identical to that tested but originating from at least one individual considered as healthy, i.e. having no pathology, at the very least not the pathology from which the individual whose biological fluid is tested is suffering, and then making it possible to evaluate the risks of said individual with respect to a value considered as normal.

According to another variant of the invention, the control identical biological fluid can be the same biological fluid as that tested, originating from the same individual but obtained in a sampling prior to that having produced the tested sample, for example before the start of a treatment, in order to be able to establish monitoring of the development of the microparticles' ability to generate plasmin for example during a treatment.

According to the invention, the first stage of the method (isolation of the microparticles, in particular the circulating microparticles present in the sample), can be carried out according to any method compatible with the isolation of such microparticles. For example there may be mentioned high-speed centrifugation or also biocapture techniques whatever the sensor support (for example antibodies, for example annexin V).

According to a preferred variant of the first stage of the method according to the invention, the microparticles, in particular the circulating microparticles, can be isolated by a succession of centrifugations and ultracentrifugations in a process according to which in a stage 1A a volume comprised between 500 µl and 5 ml, preferentially between 1 ml and 2 ml, of a sample of biological fluid, in particular a biological fluid in a flow situation, for example blood, taken previously, is centrifuged at a speed comprised between 1000 g and 2000 g, preferentially between 1200 g and 1800 g, for a time comprised between 5 minutes and 20 minutes, preferentially between 10 and 15 minutes, at a temperature comprised between 2 and 6° C., preferentially between 3 and 5° C.;

in a stage 1B, the supernatant obtained in stage 1A is centrifuged at a speed comprised between 10,000 g and 20,000 g, preferentially between 12,000 g and 15,000 g, for a time comprised between 1 minute and 5 minutes, preferentially between 2 and 3 minutes, at a temperature comprised between 2 and 6° C., preferentially between 3 and 5° C.;

in a stage 1C the supernatant obtained in stage 1B is centrifuged at a speed comprised between 15,000 g and 25,000 g, preferentially between 18,000 g and 22,000 g, for a time comprised between 45 and 120 minutes, preferentially between 60 and 100 minutes, at a temperature comprised between 2 and 6° C., preferentially between 3 and 5° C.;

in a stage 1D the pellet obtained in stage 10 is taken up in a volume comprised between 250 µl and 4 ml, preferentially between 1 and 2 ml, of phosphate buffered saline (PBS) and the mixture is centrifuged at a speed comprised between 15,000 g and 25,000 g, preferentially between 18,000 g and 22,000 g, for a time comprised between 45 and 120 minutes, preferentially between 60 and 100 minutes, at a temperature comprised between 2 and 6° C., preferentially between 3 and 5° C.;

in a stage 1E the pellet obtained in stage 1D is taken up in a volume comprised between 250 µl and 4 ml, preferentially between 1 and 2 ml, of phosphate buffered saline (PBS) and the mixture is centrifuged at a speed comprised between 15,000 g and 25,000 g, preferentially between 18,000 g and 22,000 g, for a time comprised between 45 and 120 minutes, preferentially between 60 and 100 minutes, at a temperature comprised between 2 and 6° C., preferentially between 3 and 5° C.;

in a stage 1F the pellet obtained in stage 1E is taken up in a volume comprised between 20 µl and 500 µl preferentially between 50 and 100 µl, of phosphate buffered saline (PBS).

The suspension of microparticles, in particular the circulating microparticles, obtained in stage 1F can be used immediately for analysis or can be stored preferentially at −80° C.

According to the invention, the second stage of the method (measurement of the ability of the microparticles, in particular the circulating microparticles, to generate plasmin) can be carried out directly on the quantity of microparticles obtained on completion of the first stage. Preferentially according to the invention, the second stage of the method can be carried out on a determined quantity of microparticles obtained on completion of the first stage, said quantity being able to be comprised between 10,000 and 1,000,000 microparticles, preferentially between 100,000 and 300,000 microparticles. In this case the method according to the invention can comprise an additional stage (stage 1a) of counting the microparticles obtained on completion of the first stage, said counting stage occurring between the first and the second stage of the method according to the invention.

Said counting stage can be carried out according to the invention according to any known method for counting microparticles. Advantageously, the counting of the microparticles can be carried out by flow cytometry according to the protocols used in a standard fashion in the prior art, for example those described in the French patent application FR-A-2795820, or also by a detection test based on the procoagulant activity of the microparticles (Zymuphen MP-activity, Hyphen BioMed) or also a protein assay. Preferentially according to the invention, the microparticles are counted by flow cytometry.

According to the invention, the second stage of the method, i.e. the measurement of the ability of said microparticles, in particular the circulating microparticles, isolated in stage 1 to generate plasmin can be determined either by measurement of the quantity of plasmin spontaneously present on the microparticles, or by measurement of the quantity of plasmin capable of being produced by these microparticles.

Said measurements of the plasmin can be carried out by any known method.

According to a variant of stage 2 of the method according to the invention, the measurement of the quantity of plasmin spontaneously present on the microparticles, in particular the circulating microparticles, can be carried out by any known method, such as for example an immunological measurement (FASEB J 2003, 17: 1301-3) (ELISA or Western blot) using antiplasmin(ogen) antibodies (for example TC12040, Technoclone, Austria or product 3641, American Diagnostica) or also by spectrophotometry, by absorbance reading of the sample at 405 nm using chromogenic substrates selective for plasmin (for example CBS0065, Stago).

According to another variant of stage 2 of the method according to the invention, the measurement of the quantity of plasmin capable of being produced by the microparticles, in particular the circulating microparticles, can be carried out according to the method described in Thromb Haemost 2004; 92:1066-75, in which > in a stage 2-1, plasminogen, advantageously purified, is added to the microparticles obtained in stage 1 or in stage 1a of the method according to the invention, in a final quantity comprised between 0.1 µM and 2.0 µM, preferentially between 0.5 µM and 1 µM, and a chromogenic substrate selective for plasmin, such as for example (methyl-malonyl)-hydroxypropylarginine-p-nitroanilide (CBS0065) marketed by STAGO (France), in a final quantity comprised between 0.50 mM and 1.0 mM, preferentially between 0.65 mM and 0.85 mM;
>
> in a stage 2-2 the mixture obtained in stage 2-1, is incubated for example in a drying oven, at a temperature comprised between 25° C. and 45° C., preferentially 30° C. and 40° C., for a time comprised between 30 minutes and 90 minutes, preferentially between 50 and 70 minutes and
>
> in a stage 2-3 the quantity of plasmin capable of being produced detected by photometry is measured by absorbance reading of the sample at 405 nM (for example in a 96-well plate reader such as the Dynex MR 700 microplate reader).

According to a variant of stage 2-1, a chromogenic substrate selective for plasmin can be a fluorescent substrate such as for example H-D-Val-Leu-Lys-7-amido-4-methylcoumarin (Bachem, Bubendorf, Switzerland) or D-AFK-ANSNH-iC4H9.2HB (Haematologic Technologies Inc, Vermont USA).

According to a variant of stage 2-2 the mixture obtained in stage 2-1 is deposited in a plate reader, thermostatically controlled at 37° C., which measures the plasmin-formation kinetics by measurement of the absorbance at 405 nm as a function of time.

According to the invention, the second stage of the method can be carried out on any support compatible with the incubations and the measurements to be carried out. In this connection there can be mentioned round-bottomed cups or flat-bottomed cups, for example the cups of 48- or 96-well plates made of polystyrene or polyvinyl chloride. Preferentially stage 2 of the method according to the invention is carried out in round-bottomed cups or flat-bottomed cups of 96-well plates.

According to the invention, the measurement of the quantity of plasmin capable of being produced by the microparticles, in particular the circulating microparticles, or of the quantity of plasmin spontaneously present on the microparticles, in particular the circulating microparticles, can be carried out in a final volume comprised between 25 µl and 150 µl, preferentially between 50 µl and 100 µl, adjusted for example using phosphate-buffered saline (PBS) with bovine serum albumin (BSA) added, at a concentration comprised between 1.0 and 3.0 mg/ml, preferentially between 1.5 and 2.5 mg/ml. The number of microparticles to be tested per well can be comprised between 50,000 and 400,000 particles, preferentially 100,000 to 200,000 particles per well. Advantageously, when the measurement is carried out in round-bottomed cups, the final volume is preferentially 50 µl and when the measurement is carried out in flat-bottomed cups, the final volume is preferentially 100 µl. According to the invention, the results are expressed as the quantity of plasmin produced per number of microparticles.

In a sample of biological fluid, in particular a biological fluid in a flow situation, very particularly blood, the microparticles, in particular the circulating microparticles, represent an overall population of the microparticles of which it has previously been seen that they originate from a cell blebbing and that they can be obtained from numerous different cell types. In this connection there can be mentioned microparticles obtained from endothelial cells, haematopoietic cells.

Thus, depending on the cell type from which they originate, the microparticles, in particular the circulating microparticles, will have characteristics specific to the type of cell from which they originate. On this basis it is possible to isolate the microparticles as a function of their origin and thus to generate distinct populations of microparticles of a single type. It can be useful to carry out the measurement of the plasmin activity on one particular type of microparticles only.

Thus, according to a particular embodiment of the invention, the method can also comprise a stage 1b of isolation of the microparticles as a function of their origin. This stage can be carried out after the first stage of the method according to the invention, i.e. after stage 1 or stage 1a of said method, preferentially after stage 1 and before stage 1a.

The isolation of the microparticles of interest can be carried out by any known method of the prior art. There may be mentioned in this regard a procedure of cell sorting by cytometry or also magnetic immunoseparation. Preferentially according to the invention the magnetic immunoseparation method is used.

According to yet another variant of the method according to the invention, it is possible to immobilize the microparticles isolated in stage 1 on the support on which stage 2 will be carried out. The immobilization of the microparticles can be carried out according to any known method of the prior art, in particular that described in international application WO-A-96/03655. For example it is possible to prepare the support used in stage 2 of the method according to the invention by covering its surface using a compound capable of immobilizing the microparticles, recognizing an element of the surface of said microparticles. There can be mentioned in this connection annexin V which recognizes the procoagulant phospholipids, or also the antibodies specific to the active and/or functional conformational glycoprotein complexes of the GPIIb/GPIIIa membranes, or also the adhesive receptors of the monocytes or of the LFA-1 lymphocytes or also the endothelial thrombomodulin or also CD146. According to another variant of the method according to the invention it is possible to immobilize the microparticles using a polycation such as poly-L-lysine.

A subject of the invention is also the use of microparticles, in particular the circulating microparticles, present in a sample of biological fluid, in particular a biological fluid in a flow situation, in a method for measuring the plasmin activity of said sample of biological fluid, in particular in a method for measuring the plasmin activity as described previously.

A subject of the invention is also the use of microparticles, in particular the circulating microparticles, present in a sample of biological fluid, in particular a biological fluid in a flow situation, in a diagnosis method, in an individual from whom the biological fluid originates, > of the greater or lesser risk of suffering vascular accidents caused for example by increased instability of the atheromatous plaques, or also of the greater or lesser risk for said individual with cancer of suffering a metastatic invasion, or also of the greater or lesser risk of said individual suffering a cerebral vascular accident, its haemorrhagic complications, or also its consequences for brain function.

of the risk of said individual suffering a thrombosis.

of the greater or lesser risk for said individual with a disease where the production of plasmin by the microparticles is increased such as hyperfibrinolysis or pericellular proteolysis.

Preferentially according to the invention, said diagnosis method is a method for measuring plasmin activity as described previously.

A subject of the invention is also the use of microparticles, in particular the circulating microparticles, present in a sample of biological fluid, in particular a biological fluid in a flow situation, in a method for monitoring the response of the individual from whom the biological fluid originates, to a treatment.

Preferentially according to the invention, said method of monitoring the treatment is the method for measuring plasmin activity as described previously.

The inventors have moreover been able to show that the circulating microparticles, in particular the microparticles originating from endothelial cells, contained in a biological fluid, in particular a biological fluid in a flow situation, for example blood, having a plasmin activity within the meaning of the invention, have a high resistance to inactivation, in particular to neutralization or inhibition by the inhibitors of proteolytic enzymes present in the biological fluid. This property confers upon said circulating microparticles the ability to convey the plasmin activity through the organism by the biological fluid as far as the locus where the presence of the plasmin develops its activity, without risk of inhibition, or at the very least with an extremely reduced risk of inhibition. In this connection it is known that the circulating native plasmin is rapidly inhibited in the biological fluids. Said microparticles can then be compared to a vector of the plasmin activity, which makes it possible to envisage their use as such, once purified or semi-purified. In the same way the microparticles bearing the tissue factor are potentially useful in the treatment of congenital haemorrhagic diseases such as haemophilia (Nature Medicine 2003, 9: 1020-1025).

By purified or semi-purified is meant according to the invention that the microparticles are used after undergoing at least one stage of purification.

Thus, a subject of the invention is the use of microparticles, in particular the circulating microparticles, originating from endothelial cells, purified or semi-purified, as a vector of the plasmin activity.

A subject of the invention is also the use of microparticles, in particular the circulating microparticles, in particular microparticles originating from endothelial cells, purified or semi-purified, as a medicament, in particular a medicament with proteolytic or antithrombotic activity.

Other characteristics and advantages of the invention will become apparent on reading the following examples which are given by way of illustration only, without limiting the invention in any way.

EXAMPLES

Example 1

Demonstration of the Plasmin Activity Borne by the Microparticles of Endothelial Cells in Culture 1-A: Preparation of Microparticles of Endothelial Cells:

Cells of the human microvascular endothelial line HMEC-1 (J. Invest. Dermatol. 1992; 99: 683-90) were cultured to sub-confluency in MCDB 131 medium (Invitrogen Life Technologies, Cergy Pontoise, France) to which 10% foetal calf serum (FCS) free of microparticles, 10 ng/ml of recombinant human EGF (Upstate Cell Signaling Solutions, Lake Placid, N.Y., USA) and 1 µg/ml of hydrocortisone (Sigma, St Quentin Fallavier, France) had been added.

The endothelial microparticles (EMPs) were purified from the culture medium of the HMEC-1 cells stimulated for 48 hours with 100 ng/ml of TNF-α (PeproTech Inc, Rocky Hill, N.J., USA) according to the conditions described in J. Clin. Invest. 1999 July; 104(1):93-102).

The culture supernatants were centrifuged at 4,300 g for 5 minutes in order to get rid of the cells and floating cell debris.

The supernatants were then centrifuged at 20,000 g for 120 minutes at 4° C.

The EMP pellet was then washed twice with phosphate-buffered saline (PBS) and re-suspended in PBS. Aliquots of 10 µl of EMP suspension, diluted to 1/100, were labelled with annexin V conjugated with fluorescein isothiocyanate (FITC) (Abcys, Paris, France). The EMPs were counted by flow cytometry as previously described in J. Thromb. Haemost. 2004 October; 2(10):1842-3 and French patent application FR-A-2795820.

1-B: Immobilization of the EMPS

The EMPs were immobilized on a polycation surface according to the principle of physico-chemical adsorption.

For this purpose the walls and the bottom of the round-bottomed wells of 96-well plates made of PVC were activated with 25 µg/ml poly-L-lysine (Aldrich-Sigma). Different EMP concentrations in PBS were then incubated overnight at 4° C. in the previously activated wells. The wells were then washed and the immobilized EMPs were used in the plasmin-generation test.

1-C: Plasmin-Generation Test

1-C-1: Protocol

In the round-bottomed wells of 96-well plates made of PVC, different EMP concentrations in suspension in PBS, to which 0.8% bovine serum albumin (PBSA) had been added, were incubated with 50 µl of a mixture of 1 µM plasminogen and (methyl-malonyl)-hydroxypropylarginine-p-nitroanilide (CBS0065, Stag°, Asniéres, France), chromogenic substrate selective for plasmin, at 0.75 mM.

An identical volume of supernatant from the last washing of the EMPs was used as a control.

The microplate was placed in the microplate readers and the kinetics of the appearance of the plasmin were monitored for 9 hours using a spectrophotometer suitable for reading multiwell plates (MX5000. Dynex) at 37° C. by measurement of the modifications of the absorbance at 405 nm produced by the release of the p-nitroaniline as a function of time.

1-C-2: Results

The results of these measurements are shown in the following table.

| EMP/50 μL | A405 nm/min |
|---|---|
| $10^6$ | 48.7 |
| $10^5$ | 12.9 |
| $5 \cdot 10^4$ | 4.7 |
| $10^4$ | 1.6 |
| $10^3$ | 1.1 |
| 0 | 0.5 |
| $5 \cdot 10^4$ + EACA | 0.6 |

EACA: ε-aminocaproic acid, inhibitor of the binding of plasminogen to the MPs.

1-D: Measurement of the Michaelis Constant

1-D-1: Measurement on EMPS in Suspension

1-D-1a: Protocol

In the round-bottomed wells of 96-well plates made of PVC, $2.10^5$ EMPs in suspension in PBS to which 0.8% bovine albumin serum (PBSA) had been added, were incubated with different concentrations of plasminogen (0 to 5 μM) in a final volume of 50 μl in the presence of (methyl-malonyl)-hydroxypropylarginine-p-nitroanilide (CBS0065, Stago, Asniéres, France), chromogenic substrate selective for plasmin, at 0.75 mM.

An identical volume of supernatant from the last washing of the EMPs was used as a control.

1-D-1b: Results

The results of these measurements are shown in the following table.

| Pg (μM) | A405 nm/min |
|---|---|
| 5 | 36.8 |
| 2.5 | 31.8 |
| 1.25 | 25.9 |
| 0.62 | 21.8 |
| 0.31 | 18.2 |
| 0.18 | 16.4 |
| 0 | 0.4 |

By application of the Michaelis-Menten equation, these results make it possible to determine the Michaelis constant of the plasmin-specific generation: Km=0.122 μM 1-D-2: Measurement on Immobilized EMPS 1-D-2a: Protocol The microparticles were immobilized in the wells as indicated above (1-B Immobilization of microparticles).

The plasminogen and the chromogenic substrate were added to the immobilized microparticles according to the same protocol as for the EMPs in suspension.

The kinetics of plasmin formation were detected in a microplate reader by measurement of the absorbance at 405 nm.

This variant makes it possible after detection of the activation kinetics to measure the plasmin bound to the immobilized microparticles. To this end, the plates are washed with PBSA and the plasmin fixed to the immobilized microparticles was detected by the addition of 50 μl/well of 0.325 mM of CBS0065 and measurement of modifications of the absorbance at 405 nm.

1-D-2b: Results

| EMP/50 μL | A405 nm/min |
|---|---|
| $2 \cdot 10^5$ | 4.6 |
| $10^5$ | 2.3 |
| $7,5 \cdot 10^4$ | 1.5 |
| $5 \cdot 10^4$ | 0.8 |
| $2,5 \cdot 10^4$ | 0.6 |

1-E: Conclusion

These results show that the formation of plasmin by the microparticles is a function of the number of microparticles added to the wells or at a fixed concentration of microparticles of the concentration of plasminogen added. These results also show that the effect of the microparticles is due to the presence of an activator of the plasminogen present on the microparticles.

Example 2

Demonstration of the Plasmin Activity Borne by the Microparticles In Vivo

2-A: Protocol

Starting with a sample of total blood previously obtained from an individual having an autoimmune pathology at risk of thrombosis, the microparticles were isolated according to the following method:

(stage 1A) 2 ml of said blood sample was centrifuged at a speed of 1,500 g, for 10 minutes, at a temperature of 4° C.;

(stage 1B) the supernatant obtained in stage 1A was centrifuged at a speed of 17,500 g, for 2 minutes, at a temperature of 4° C.;

(stage 1C) the supernatant obtained in stage 1B was centrifuged at a speed of 17,500 g, for 90 minutes, at a temperature of 4° C.;

(stage 1D) the pellet obtained in stage 1C was taken up in 1,000 μl of phosphate buffered saline (PBS) and the mixture was centrifuged at a speed of 17,500 g, for 90 minutes, at a temperature of 4° C.;

(stage 1E) the pellet obtained in stage 1D was taken up in 1,000 μl of phosphate buffered saline (PBS) and the mixture was centrifuged at a speed of 17,500 g, for 90 minutes, at a temperature of 4° C.;

(stage 1F) the pellet obtained in stage 1E was taken up in 50 μl of phosphate buffered saline (PBS) for storage and subsequent use.

The microparticles thus obtained in stage 1F are counted by flow cytometry.

In a round-bottomed cup of a 96-well plate (Vinyl alphanumeric U bottom plates, Ref. 2101, Thermo), in a final volume of 50 μl, adjusted if necessary with phosphate-buffered saline (PBS) with bovine serum albumin added at a final concentration of 2 mg/ml, purified plasminogen (American Diagnostica, Hyphen) at a final concentration of 0.5 μM (or 1 μM) and CBS0065 (STAGO) at a final concentration of 0.75 mM are added to 200,000 microparticles previously obtained and stored in PBS with bovine serum albumin added at a final concentration of 2 mg/ml.

On completion of the addition of the plasminogen and the chromogenic substrate to the microparticles in a final volume of 50 μl in the 96-well plate, said plate is placed directly in the photometer which is thermostatically controlled at 37° C.

(MX5000, Dynex) in order to detect the variation in absorbance at 405 nm as a function of time over 4 to 8 hours.

The plasmin activity of a control sample, originating from a subject free from risk of thrombosis is measured in parallel under the same conditions. The quantity of plasmin produced by the microparticles is calculated with respect to a reference curve produced with variable concentrations of plasmin (0 to 20 nM).

2-6: Results

| P | A |
|---|---|
| 1 | 1.35 |
| 2 | 1.8 |
| 3 | 0.7 |
| 4 | 0.5 |
| 5 | 3.5 |
| 6 | 1.0 |
| 7 | 0.6 |
| 8 | 2.8 |
| 9 | 0.4 |
| 10 | 0.7 |
| 11 | 1.2 |
| 12 | 9.05 |
| 13 | 1.5 |
| 14 | 1.05 |
| 15 | 1.8 |
| 16 | 2.15 |
| 17 | 3.75 |
| 18 | 7.5 |
| 19 | 6.5 |
| 20 | 0.85 |
| 21 | 1.5 |
| 22 | 0.9 |

A: absorbance (405 nm/min);
P = patient

2-C: Conclusion

These results show that the circulating microparticles isolated from the plasma of a subject with an autoimmune disease, generate plasmin as do the particles of the prototype tested in vitro. These results also show that the effect of the microparticles produced in vivo depends on the presence of added plasminogen.

The invention claimed is:

1. Method for measuring the plasmin activity of microparticles, in a sample of biological fluid which is blood or a blood component, taken previously, comprising the following steps:
   in a first stage isolating said microparticles present in said sample according to a method comprising,
      centrifuging in a stage 1A in a volume between 500 µl and 5 ml, of a sample of biological fluid, taken previously, at a speed between 1,000 g and 2,000 g, for a time between 5 minutes and 20 minutes, at a temperature between 2 and 6° C. to obtain a first supernatant;
      centrifuging in a stage 1B the supernatant obtained in stage 1A at a speed between 10,000 g and 20,000 g, for a time between 1 minute and 5 minutes at a temperature between 2 and 6° C. to obtain a second supernatant;
      centrifuging in a stage 1C the second supernatant obtained in stage 1B at a speed between 15,000 g and 25,000 g, for a time between 45 and 120 minutes, at a temperature between 2 and 6° C., to obtain a pellet;
      in a stage 1D, taking up the pellet obtained in stage 1C in a volume of between 250 µl and 4 ml of phosphate buffered saline and centrifuging the mixture at a speed between 15,000 g and 25,000 g for between 45 and 120 minutes at a temperature between 2 and 6° C.;
      in a stage 1E, taking up the pellet obtained in stage 1D in a volume of between 250 µl and 4 ml of phosphate buffered saline and centrifuging the mixture at a speed between 15,000 g and 25,000 g for between 45 and 120 minutes at a temperature between 2 and 6° C.;
      in a stage 1F, taking up of the pellet obtained in stage 1E in a volume of between 20 µl and 500 µl of phosphate buffered saline;
   in a second stage, measuring the ability of said microparticles isolated in stage 1 to generate plasmin, and
   in a third stage, comparing the result of the measurement obtained in the second stage with the result of an identical measurement carried out under the same conditions on a control sample of identical biological fluid.

2. Method according to claim 1, characterized in that said control identical biological fluid is a biological fluid identical to that tested but originating from at least one individual considered as healthy, the control fluid or is the same biological fluid as that tested, originating from the same individual but obtained in a sampling prior to that having produced the tested sample.

3. Method according to claim 1, characterized in that the second stage of said method involving measurement of the ability of said microparticles to generate plasmin, is carried out directly on the quantity or on a determined quantity of microparticles obtained on completion of the first stage.

4. Method according to claim 3, characterized in that said quantity is between 10,000 and 1,000,000 microparticles.

5. The method of claim 4, wherein said quantity is between 100,000 and 300,000 microparticles.

6. Method according to claim 1, characterized in that the method comprises an additional stage of counting said microparticles obtained on completion of the first stage, said counting stage occurring between the first and the second stage of the method.

7. Method according to claim 6, characterized in that the counting of said microparticles is carried out by flow cytometry.

8. Method according to claim 1, characterized in that the second stage of said method is determined either by measurement of the quantity of plasmin spontaneously present on said microparticles, or by measurement of the quantity of plasmin capable of being produced by these microparticles.

9. Method according to claim 8, characterized in that the measurement of the quantity of plasmin spontaneously present on said microparticles is carried out by an immunological measurement using antiplasmin or antiplasminogen antibodies or by spectrophotometry by absorbance reading of the sample at 405 nm using chromogenic substrates selective for plasmins.

10. Method according to claim 8, characterized in that measurement of the quantity of plasmin capable of being produced by said microparticles is carried out according to a process in which
   in a stage 2-1, adding of plasminogen to microparticles obtained in stage 1 or in stage 1a of said method, in a final quantity of between 0.1 µM and 2.0 µM, and a chromogenic substrate selective for plasmin, in a final quantity comprised between 0.50 mM and 1.0 mM;
   in a stage 2-2 incubating of the mixture obtained in stage 2-1, at a temperature between 25° C. and 45° C., for a time between 30 minutes and 90 minutes and
   in a stage 2-3 detecting of quantity of plasmin capable of being produced by photometry by absorbance reading of the sample at 405 nM.

11. The method of claim 10, wherein
in stage 2-1, the plasminogen is purified and the microparticles are added in a final quantity of between 0.5 µM and 1 µM, and the chromogenic substrate selected for plasma is added in a final quantity between 0.65 mM and 0.85 mM; and/or
in stage 2-2, the incubation is conducted in a drying oven at a temperature between 30° C. and 40° C. for between 50 and 70 minutes.

12. Method according to claim 10, characterized in that in stage 2-1, the plasmin-selective substrate is a fluorescent substrate optionally H-D-Val-Leu-Lys-7-amido-4-methyl-coumarin or D-AFK-ANSNH-iC4H9.2HB.

13. Method according to claim 1, characterized in that the second stage of said method is carried out in a final volume between 25 µl and 150 µl.

14. Method according to claim 1, characterized in that the second stage of said method, i.e. the measurement of the ability of said microparticles isolated in stage 1 to generate plasmin, is carried out in a phosphate-buffered saline with bovine serum albumin added, at a concentration between 1.0 and 3.0 mg/ml.

15. Method according to claim 1, characterized in that the method also comprises a stage 1b of isolation of said microparticles as a function of their origin.

16. Method according to claim 1, characterized in that said microparticles isolated in stage 1 are immobilized on a support on which stage 2 is carried out.

17. Method according to claim 16, characterized in that said microparticles isolated in stage 1 are immobilized on the support using a compound capable of immobilizing said microparticles, said compound being previously fixed to the surface of said support.

18. Method according to claim 17, characterized in that said compound capable of immobilizing said microparticles is chosen from annexin V, antibodies specific to active and/or functional conformational glycoprotein complexes of the GPIIb/GPIIIa membranes, adhesive receptors of monocytes or of LFA-1 lymphocytes, endothelial thrombomodulin, or also CD 146 or a polycation such as poly-L-lysine.

19. Method according to claim 18, characterized in that the method for measuring the plasmin activity of said sample of biological fluid comprises,
in a first stage isolating of said microparticles present in said sample,
in a second stage, measuring of the ability of said microparticles isolated in stage 1 to generate plasmin and
in a third stage comparing of the result of the measurement obtained in the second stage with the result of an identical measurement carried out under the same conditions on a control sample of identical biological fluid.

20. The method of claim 1, wherein
in stage 1A the centrifuging is carried out between 1,200 and 1,800 g, for 10-15 minutes at 3-5° C.; and/or
in stage 1B the supernatant is centrifuged between 1,200 and 1,500 g, for 2-3 minutes, at 3-5° C.; and/or
in stage 1C the supernatant is centrifuged at between 1,800-2,200 g, for 60-100 minutes at 3-5° C.; and/or
in stage 1D the mixture is centrifuged at between 1,800-2,200 g, for 60-100 minutes at 3-5° C.; and/or
in stage 1E the mixture is centrifuged at between 1,800-2,200 g, for 60-100 minutes at 3-5° C.

* * * * *

UNITED STATES PATENT AND TRADEMARK OFFICE
CERTIFICATE OF CORRECTION

PATENT NO. : 8,541,189 B2
APPLICATION NO. : 12/663393
DATED : September 24, 2013
INVENTOR(S) : Angles Cano et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 803 days.

Signed and Sealed this
Fifteenth Day of September, 2015

Michelle K. Lee
*Director of the United States Patent and Trademark Office*